(12) United States Patent
Sommer

(10) Patent No.: US 11,942,211 B2
(45) Date of Patent: Mar. 26, 2024

(54) METHOD AND SYSTEM FOR GENERATING A REPORT

(71) Applicant: SMART REPORTING GMBH, Munich (DE)

(72) Inventor: Wieland Sommer, Munich (DE)

(73) Assignee: SMART REPORTING GMBH (DE)

(*) Notice: Subject to any disclaimer, the term of this patent is extended or adjusted under 35 U.S.C. 154(b) by 482 days.

(21) Appl. No.: 17/280,024

(22) PCT Filed: Sep. 26, 2019

(86) PCT No.: PCT/EP2019/075995
§ 371 (c)(1),
(2) Date: Mar. 25, 2021

(87) PCT Pub. No.: WO2020/074263
PCT Pub. Date: Apr. 16, 2020

(65) Prior Publication Data
US 2021/0398629 A1    Dec. 23, 2021

(30) Foreign Application Priority Data

Oct. 8, 2018   (EP) ..................................... 18199170

(51) Int. Cl.
*G16H 30/40*    (2018.01)
*G06F 18/40*    (2023.01)
(Continued)

(52) U.S. Cl.
CPC ............. *G16H 30/40* (2018.01); *G06F 18/41* (2023.01); *G06V 10/7788* (2022.01);
(Continued)

(58) Field of Classification Search
CPC ........ G16H 15/00; G16H 30/40; G16H 50/20; G16H 50/70
(Continued)

(56) References Cited

U.S. PATENT DOCUMENTS

2004/0083217 A1    4/2004  Brackett et al.
2004/0181431 A1    9/2004  Kuth et al.
(Continued)

FOREIGN PATENT DOCUMENTS

KR    20080021723 A  *  3/2008
WO    WO 2016/135100 A1   9/2016

OTHER PUBLICATIONS

PCT International Search Report and Written Opinion, PCT/EP2019/075995, dated Nov. 18, 2019, 15 pages.
European Patent Office, Communication Pursuant to Article 94(3) EPC, Application No. 18199170.4, dated Apr. 6, 2023, 10 pages.

*Primary Examiner* — Jonathon A. Szumny
(74) *Attorney, Agent, or Firm* — QUARLES & BRADY LLP

(57) ABSTRACT

The present invention relates to a method for generating a report (50) comprising receiving a user input to thereby generate at least one final finding (24); automatically generating the report (50) based on the at least one final finding (24); and utilizing the at least one final finding (24) to train at least one algorithm (12), wherein the at least one algorithm (12) is configured to generate at least one machine finding (22). The present invention also relates to a corresponding system and use.

12 Claims, 5 Drawing Sheets

(51) Int. Cl.
*G06V 10/778* (2022.01)
*G16H 15/00* (2018.01)
*G16H 30/20* (2018.01)
*G16H 50/20* (2018.01)
*G16H 50/70* (2018.01)
*H04L 9/40* (2022.01)

(52) U.S. Cl.
CPC .............. *G16H 15/00* (2018.01); *G16H 30/20* (2018.01); *G16H 50/20* (2018.01); *G16H 50/70* (2018.01); *H04L 63/0428* (2013.01)

(58) Field of Classification Search
USPC ............................................................ 705/2
See application file for complete search history.

(56) References Cited

U.S. PATENT DOCUMENTS

| | | | |
|---|---|---|---|
| 2005/0010445 A1* | 1/2005 | Krishnan | G16H 50/20 706/45 |
| 2015/0088544 A1* | 3/2015 | Goldberg | G16H 80/00 705/2 |
| 2016/0048956 A1 | 2/2016 | Bryan et al. | |
| 2016/0364857 A1* | 12/2016 | Reicher | G06T 7/0014 |
| 2017/0018076 A1* | 1/2017 | Middlebrooks | G06F 18/217 |
| 2018/0068438 A1* | 3/2018 | DeVries | G06V 10/82 |
| 2018/0137244 A1* | 5/2018 | Sorenson | A61B 8/565 |
| 2019/0392944 A1* | 12/2019 | Samset | G16H 30/40 |
| 2020/0004561 A1* | 1/2020 | Kottler | G16H 20/00 |

* cited by examiner

Fig. 2 (a)

| Lung enlarged? | Not specified | | Not checked ✓ |
| | Yes ✓ | | Checked |
| | No | | |

| Lung enlarged? | Not specified | | Not checked |
| | Yes ✓ | | Checked ✓ |
| | No | | |

| Lung enlarged? | Not specified | | Not checked |
| | Yes | | Checked ✓ |
| | No ✓ | | |

| Which type of enlarged lung is it? | Not specified | Not checked |
| | Tumor | Checked ✓ |
| | Hyperinflated ✓ | |

| Which type of tumor is it? | Not specified | Not checked |
| | Sarcoma | Checked ✓ |
| | Carcinoma ✓ | |

METHOD AND SYSTEM FOR GENERATING A REPORT

CROSS-REFERENCE TO RELATED APPLICATIONS

This application is a national stage of International Application No. PCT/EP2019/075995, filed Sep. 26, 2019, which claims the benefit of European Application No. 18199170.4, filed Oct. 8, 2018, in the European Patent Office, the disclosures of which are incorporated herein by reference.

The present invention generally lies in the field of generating reports, such as medical reports.

Medical reports summarize findings of medical personnel, such as doctors. As an example, a radiological report will shortly be discussed. A radiologist typically prepares a radiological report after an examination of an image, or a series of images, which images may be obtained, e.g., by means of X-rays. In a radiological report, the radiologist summarizes their findings, e.g., with regard to organs, abnormalities, and potentially also indicates physical conditions of a patient to be examined. Such a report may then be transmitted to another medical doctor being an expert in another medical field, e.g., a surgeon, or an internist, for further treatment.

Typically, such medical reports are written by medical personnel, e.g., by the doctor (in the above example: by the radiologist). The medical personnel either enters text into a computer (e.g., by using word or other computer programs), notes down the findings by hand, or dictates the findings. In the latter two examples, other personnel, e.g., doctor's assistants may then also convert these findings, e.g., to a word document. Thus, a medical report based on a free text written or dictated by the doctor is generated. This typical solution may have certain drawbacks and shortcomings. Firstly, such reports bear the risk of the doctor forgetting to include relevant information in the report. There is no entity checking such reports for completeness. Further, medical reports generated in this way may be substantially non-uniform. That is, e.g., when the same radiological image is examined by a plurality of radiologists, the generated medical reports (for the same images) may differ considerably. Such differentiation may be based on different aspects: First, the findings of the radiologists may differ from one another. E.g., one radiologist may consider an organ to be enlarged and this being an indication of a medical condition, while another radiologist may consider the organ to be at a normal size and not to be an indication of a medical condition. Second, even if two doctors generally agree on the findings, the findings may be presented in a different manner. For example, even if two radiologists may be of the opinion that an organ is enlarged and indicates a medical condition, one may present this finding in a definite manner (e.g., "The organ A is enlarged. Thus, the medical condition B exists."), while another doctor may present their identical finding in a different manner (e.g., "The organ A is enlarged. Thus, there is a high likelihood of the medical condition B."). Finally, there may also be differences in writing styles between different doctors. All this may render medical reports, even if based on the same "input", very non-uniform. It will be understood that this is not ideal for further using such medical reports. In the above example, another doctor (e.g., an internist or a surgeon) is provided with the medical report of the radiologist and bases their treatment on this medical report. For this further doctor, it would be ideal if results of the medical reports were as uniform as possible (when referring to the same "input"). It will be understood that the lack of uniformity makes it harder for the further doctor to study reports (as they first have to interpret the report), thereby resulting in sub-ideal treatment results.

In other words, medical examination of a patient generates a diverse amount of data that medical personnel need to bear with. These data may significantly differ in terms of content and complexity. Typically, processing and reporting medical findings implies a heavy involvement of medical personnel, and therefore the interpretation of the different information of a medical examination relies on their knowledge and judgement. This typical approach brings along some inconveniences. First, the dependency on the knowledge and judgement of medical personnel may also vary according to their experience. In other words, less experience medical personnel may overlook certain patterns that may be of importance for the right and complete reporting of a medical finding. Further, the medical personnel may encounter a rare and/or infrequent information that could also be misidentified by more than one medical practitioner. Second, the heavy involvement of medical personnel may result in different reporting styles (e.g. writing style, wordings, grade of details). Such differences may result in reports that are difficult to understand and/or impossible to further proceed by a further referring medical practitioner. Therefore, a non-standardized report generation procedure, medical communications may drastically differ one to another. In other words, every single medical personnel interpret the image data based on their own knowledge and experience, and subsequently elaborates a report following their individual criteria. As a result, the summarized data provided to the referring clinician may lack consistency of content depending on the medical personnel that reported it.

Furthermore, an unstructured interpretation of image data may lead to misunderstanding of different medical conditions, which consequently may lead to suboptimal treatment of patients or in the worst case scenarios, it may also result in a mistreatment. Additionally, the accuracy of image data interpretation also varies proportionally to the degree of expertise and practical experience of the medical professional in charge of interpreting and reporting the information. Moreover, the misinterpretation of a given data may, for example, go unnoticed.

WO 2016/135100 A1 already discloses a solution for electronically producing at least a part of a medical report. In simple words, this document discloses a question tree, and a report node tree. A user may input answers to the questions (e.g., "Was a scan performed?") and a part of a report (e.g., "A scan was performed") may be generated based on the answers to the questions. Thus, this disclosure already increases the uniformity of reports, as the medical doctor only has to answer questions and the medical report will then be generated automatically. Thus, if two doctors provide the same answers to the questions, two identical reports may be generated. This already increases the uniformity of medical reports and facilitates studying of such medical reports for subsequent usage.

While the prior art may be satisfactory in some instances, it still has certain shortcomings and disadvantages with regard to reproducibility and consistency of generating reports. Furthermore, the prior art may still be far from optimal as regards time efficiency.

In light of the above, it is an object of the present invention to overcome or at least alleviate the shortcomings and disadvantages of the prior art. In other words, it is an object of the present invention to provide a technology being improved with regard to reproducibility, consistency and/or time efficiency of generating reports.

The objects are met by the present invention.

In a first embodiment, the present invention relates to a method for generating a report. The method comprises receiving a user input to thereby generate at least one final finding; automatically generating the report based on the at least one final finding; and utilizing the at least one final finding to train at least one algorithm, wherein the at least one algorithm is configured to generate at least one machine finding.

In other words, a user provides an input and a system may generate a final finding based on this input. For example, the user may be prompted to provide an input to the question: "Is the lung enlarged?", and the user's input may be "Yes.". The system may thus generate the final finding "The lung is enlarged.". The final finding will also be referred to as a human-based finding, as it was generated (or at least approved) by a human.

It will be understood that the user input may have a plurality of data points and that thus, there may also be a plurality of final findings.

Based on these one or more final findings, a report, such as a medical report, may be automatically generated. By automatically generating the report, the report is very reproducible and can therefore be more readily used by another user. That is, a first user (typically medical personnel, such as a doctor) inputs information resulting in a final finding, which is used to generate a report. The user is thus motivated to provide the input, as they benefit from the report being generated.

However, the final finding is not only used to generate the report, but also to train one or more algorithms.

In the above discussed example (with the question: "Is the lung enlarged?"), a typical use scenario is a radiologist reviewing an image. After providing the user input and thus the final finding ("The lung is enlarged."), the respective image is "annotated". That is, one has the feedback by an expert that the respective image depicts an enlarged lung.

Such annotations based on the final findings may be crucial to train algorithms, such as pattern recognition algorithms, trying to find patterns in images.

One benefit of the present technology is that trained personnel (such as doctors) provide input (and thus annotate information) to generate a report, but that this annotation is also used to further train algorithms to improve them.

Such training of algorithms may lead to superior pattern recognition in subsequent steps, and may thus overall lead to better automated detection of patterns (e.g., conditions), thus improving the reproducibility and consistency of reports, and also allowing them to be generated faster.

The method may further comprise outputting at least one output machine finding to a user; and further the user input may be related to the at least one output machine finding output to the user.

Above, it has been discussed that a user may provide an input and that a final finding (also referred to as a human based finding) is thus generated. However, e.g., prior to this, it is also possible that an output machine finding (which may also be referred to as a preliminary or initial finding) is generated and output to a user. In the above example, a medical image may first be subjected to one or more algorithms, such as pattern recognition algorithms.

They may generate a output machine finding, such as "The lung is enlarged.". Such a output machine finding may be output to the user and the user may decide whether they approve it.

It will be understood that the present technology utilizes the one or more final findings to train the algorithms, which algorithms are configured to generate machine findings.

In embodiments of the present embodiment, one such machine finding is output to the user, and is thus referred to as "output machine finding". It should be understood that the output machine finding may be comprised in the machine findings. That is, the machine finding generated by an algorithm A may be output to the user, and reviewed by the user to thus generate a final finding. This final finding can then be fed back to train this very algorithm A. However, it is also possible to use this final finding to train another algorithm. Thus, the at least output machine finding can be, but does not necessarily have to be, identical to the at least one machine finding. Corresponding considerations apply for the discussed algorithms.

The method may carried out by a data processing system.

The method may further comprise at least one algorithm generating the at least one output machine finding.

The at least one output machine finding may be generated based on input data.

The input data may be medical data.

The medical data nay comprise medical imaging data.

The medical imaging data may be data retrieved by at least one of X-ray, magnetic resonance imaging, ultrasound, endoscopy, elastography, tactile imaging, thermography, medical photography and nuclear medicine functional imaging techniques as positron emission tomography (PET) and Single-photon emission computed tomography (SPECT).

The medical data may comprise data based on electroencephalography (EEG), magnetoencephalography (MEG), and/or electrocardiography (ECG).

The report may be a medical report.

The at least one output machine finding may be output to the user before receiving the user input.

The at least one output machine finding may be a plurality of output machine findings.

The method may further comprise storing the output machine findings in a tree structure.

This may be a very viable way of logically storing the output machine findings in a computer readable format.

The at least one final finding may be a plurality of final findings.

The method may further comprise storing the final findings in a tree structure.

The user input may comprise a plurality of input data points.

The input data points may be computer-readable input data points.

The input data points may comprise at least one select data point with one or more predetermined select options, and in the step of receiving a user input, the user may select one or more of the select options.

As a mere example, the user may be presented with the question: "Is the lung enlarged?" and the user may answer any of the following select options: "Yes", "No". Having such a limited number of predetermined options may allow for a very defined and thus reproducible data input.

The input data points may comprise at least one free text data point, and in the step of receiving a user input, the user may provide a text.

That is, as one alternative to the select data point, the user may also input their input in as a free text, e.g., by typing in the text or by speaking the text into a microphone.

The input data points may comprise at least one probability input data point, and at least one final finding may be a probability finding.

In embodiments of the present invention, at least some input data points, i.e., at least some parts of the user input, may not be definite input, but a probability input. That is, instead of a user providing definite input (e.g., "The lung is enlarged."), the user may provide the input as a probability. For example, the user may be presented with an output machine finding: "Probability that the lung is enlarged: 80%.", and the user may then approve or alter the probability. It will be understood that this may be done both by means of a free text input and also by means of a select data point input. In the latter case, intervals or approximate select options (such as >95%, ~75%, ~50%, ~25%, <5%) may be provided.

It will be understood that there may be a plurality of situations where a probability input may be more suitable. For example, when a doctor examines a medical image, it may be more appropriate to assign likelihoods to certain observations than to state a definite observation.

Thus, the user may be prompted to provide such probabilistic feedback. This may be beneficial, as it forces different users to provide more consistent feedback. Without any technological means, it is well possible that two professionals describe the same finding differently, e.g., one as a definite finding and the other as a probable finding. This is overcome by the present technology.

Furthermore, it will also be understood that such probabilistic feedback may also be beneficial when training the algorithms, as it provides more information than a mere binary finding.

At least one output machine finding may be a probability finding.

It will be understood that the above rationales relating to the probability finding for the input data points also apply to the output machine finding(s).

The at least one algorithm may comprise a pattern recognition algorithm.

The data processing system may comprise a user terminal and a server.

The user input may be received by the user terminal.

The report may be generated by the user terminal

In other words, the report may be generated locally by the user terminal. This may be beneficial, as the report may thus be generated not requiring constant communication with an external entity. Thus, the report may be generated promptly, and sometimes even in real time.

This may be beneficial, as a preliminary or current report (or a section thereof) may also be continuously displayed to the user. Thus, the user may get immediate feedback in case they approve or disapprove any of the output machine findings.

The step of utilizing the at least one final finding to train at least one algorithm may be performed by the server.

That is, in embodiments of the present invention, training of the algorithm(s) and generating the report may be performed by different data processing devices. This may be beneficial, as it may allow the server (which may have more computing power) to run the algorithms, while allowing the local user terminal to rapidly generate the report.

The method may further comprise generating the at least one output machine finding.

The step of generating the at least one output machine finding may be performed by the server.

The user terminal may output the at least one output machine finding to the user.

The data processing system may further comprise a data input terminal.

The method may further comprise inputting the input data by means of the data input terminal.

That is, a still further data processing device may be used to input the input data.

The method may further comprise sending the input data from the data input terminal to the server.

The input data may be sent encrypted from the data input terminal to the server.

The input data may be sent end-to-end encrypted.

This may allow a secure communication of the input data. This may be particularly beneficial if the input data is confidential (such as medical data, e.g., medical imaging data of a patient).

The at least one output machine finding may be sent from the server to the user terminal.

The at least one final finding may be sent from the user terminal to the server.

At least a part of the communication between the server and the user terminal may be encrypted.

At least a part of the communication between the server and the user terminal may be end-to-end encrypted.

The present invention also relates to a data processing system. The system is configured to generate a report. The system comprises a receiving component for receiving a user input to thereby generate at least one final finding; a generating component for automatically generating the report based on the at least one final finding; and a utilizing component for utilizing the at least one final finding to train at least one algorithm, wherein the at least one algorithm is configured to generate at least one machine finding.

The system may further comprise an outputting component configured to output at least one output machine finding to a user.

The system may further comprise at least one algorithm configured to generate the at least one output machine finding.

The at least one output machine finding may be based on input data that is preferably fed into the algorithm.

The input data may be medical data.

The medical data may comprise medical imaging data.

The medical imaging data may be data retrieved by at least one of X-ray, magnetic resonance imaging, ultrasound, endoscopy, elastography, tactile imaging, thermography, medical photography and nuclear medicine functional imaging techniques as positron emission tomography (PET) and Single-photon emission computed tomography (SPECT).

The medical data may comprise data based on electroencephalography (EEG), magnetoencephalography (MEG), and/or electrocardiography (ECG).

The report may be a medical report.

The report may be in computer readable form.

The system may comprise a user terminal.

The user terminal may comprise the receiving component.

The user terminal may comprise the outputting component.

The user terminal may comprise the generating component.

The system may comprise a server.

The server may comprise the utilizing component.

The system may further comprise a data input terminal.

The data input terminal may be configured to receive the input data.

The system may be configured to carry out the method as discussed above.

The present invention also relates to a computer program comprising instructions which, when the program is executed by a computer, cause the computer to carry out the method as discussed above.

The present invention also relates to a non-transient computer-readable medium comprising instructions which, when executed by a computer, cause the computer to carry out the method as discussed above.

The present invention also relates to a use of the system as discussed above.

The use may be for carrying out the method as discussed above.

It will be understood that the system, the computer program, the computer-readable medium, and the use may comprise advantages and benefits corresponding to the ones discussed above with regard to method.

Furthermore, it will be understood that the present invention also relies on the following observations. In medical diagnosis, reports are required containing customized structures and information relevant to every patient. Reports are also required to carry relevant information relating to each individual medical procedure involved in the diagnosis of a disease or a medical condition. There are attempts to solve the problematic of unstructured reports, however, only partially successful results have been achieved. Due to the increasing amount and diversity of information that medical professionals should deal with, the present technology provides a tool able to (semi) automatically generate reports. Moreover, the present invention is also superior with regard to assisting in the standardization of the data interpretation of medical data, and is able to adjust itself to the constantly evolving requirements of medical diagnosis.

In current medical diagnosis, patients are typical subjected to a plurality of medical examinations, which may yield results represented by several means. Frequent means of retrieving results of medical examinations are medical imaging data. Patients may undergo medical examinations, which may include at least one or more methods and techniques such as X-ray, magnetic resonance imaging, ultrasound, endoscopy, elastography, tactile imaging, thermography, medical photography, nuclear medicine functional imaging techniques as positron emission tomography (PET), and Single-photon emission computed tomography (SPECT). Additional means of delivering medical data are graphical representation of electrical activities and/or magnetic fields, which may be used to monitor and/or map the activity of specific given organs, such as brains or hearts. Such graphical representations may comprise medical data based on electroencephalography (EEG), magnetoencephalography (MEG), and/or electrocardiography (ECG).

The medical data retrieved from different examination methods and/or techniques are of diverse complexity and the information therein may contain signs of a plurality of medical conditions. The generated results may be stored or processed, e.g. as image data, and are provided in such a format that makes feasible further processing by algorithms. Hence, the medical data may also be referred to as input data. The medical examinations may yield medical data not only in computer readable and/or any other kind processable form, but may also, after a series of processes, generate information readable by a specialized natural entity, e.g. a medical personnel, i.e. doctors. This final readable information may also be referred to as reports. Such reports are generated by outputting at least one machine finding and possibly deliver it to a user.

In a further step, the input data may undergo data analysis. The aim of the data analysis is to locate, identify and/or recognized reproducible features in given medical data. Such a processing may yield information related to medical conditions, which may also be referred to as findings. Further processing of the findings, as explained, may be summarized in a final output, which may be referred to as medical report, or simply as a report.

In embodiments, the present invention provides a method for generating such reports based on outputting at least one machine finding to a user. The generation of a finding may be conceived in two stages. First, after an algorithm (or a plurality of algorithms) identifies patterns in a medical data, and assigns them to a potential medical condition, a first set of findings is generated. This initial set of findings may also be referred to as machine finding. Second, the machine findings are made available to a user (e.g. a doctor specialist) for verification of the veracity of the machine finding. This second set of user-verified findings may also be referred to as human-based findings. Hence, the present invention also comprises receiving a user input to thereby generate at least one final finding or human-based finding. Once a final finding is obtained, the method may allow utilizing this human-based finding, on the one hand, to generate a final medical report, and on the other hand, to train at least one of the algorithms involved in the process of the medical data. It will be understood that this algorithm (or plurality of algorithms) is also configured to generate the at least one machine finding. In simple words, the algorithms are in charge of executing the data processing, and therefore, are part of the data processing system, which carries out the method.

One embodiment of the present invention may comprise a data processing system configured to operate the system, at least partially. The data processing may be executed by a given algorithm and/or a plurality of algorithms, which may, as fundamental function, be configured to generate a machine finding or a plurality of machine findings. In other words, an embodiment of the present invention may comprise algorithms, which may break down the medical data into smaller components. The medical imaging data (disaggregated into simpler information arrangements by given algorithms) may be linked to a potential medical condition. The combination of an algorithm (and/or a plurality of algorithms) identifying a pattern in a medical data, and assigning them to a potential medical condition, may also be referred to as machine finding. Put in simple words, the results yield by the algorithms after processing a medical data may be called machine findings. It will be understood that the machine findings have not yet been verified by any natural entity, i.e. a medical personnel. However, every machine finding is based at least on one of the medical data that is preferably fed into the algorithms.

The unbundling of medical data into information units may also be referred to as scanning of the medical data, medical data analysis, medical data processing, or pattern recognition. Therefore, it will be understood that the medical data processing may use as input every medical imaging data containing in the medical data, and the medical data may further contain other types of data representation and/or data storage, such as electrical and/or magnetic signals. In other words, the data processing may involve running a series of algorithms, which perform a thorough screening of the medical data and identifies the different medical patterns contained therein. The pattern recognition can involve, in a first step, the identification of zonal and/or spatial information in the medical data. In a second step, the algorithms can isolate the information into small information clusters or units. Further, the identified features or arrangements are correlated with a given clinical condition. Moreover, the disaggregated data may display more than one pattern and it may therefore be treated as input for as many different data groups or information clusters as it may belong to, and the disaggregate data may be associated at least to one data group or information clusters. The data group or information cluster may represent a set of clinical conditions.

The present invention also provides a computer-implemented system for generating a report by means of an outputting component, which is configured to output at least one machine finding to a user. Further, the computer-implemented system may comprise a receiving component for receiving a user input on the at least one machine finding to thereby generate at least one final finding. Moreover, the system may comprise a generating component for automatically generating a report base on the at least one final finding.

In one embodiment of the present invention, the system may also comprise a utilizing component for utilizing the at least one final finding to train at least one algorithm, which is configured to generate at least one machine finding.

Moreover, some disaggregated input data may trigger a list of options from which the user can select. Therefore, some disaggregated data may be associated to at least one option related to at least one medical condition, and according to the option selected for a given option or parameter, a subsequent action may be initialized. In other words, according to the option selected for a first disaggregated data, it might be required to the user to further select other options or parameters.

The data processing may comprise a series of steps that may take place following a determined order or more than one action or sub action being performed simultaneously. In one embodiment, the data processing may comprise an in-deep screening of the disaggregated medical data. Thus, the data processing may also include performing, inter alia, statistical analysis of the identified patterns, comparison of the identified pattern to an existing set of clinical conditions, and further statistical computing. Subsequently, the analyzed medical data may be subjected to further data processing, that may comprise, for example, classifying and organizing the analyzed medical data into a set of findings available to a user. In simple terms, the data processing may also comprise the distribution and allocation of the data obtained from processing the medical imaging data to a correspondent existing group of clinical conditions. In one embodiment, therefore, a set of an existing group of clinical conditions may also be referred to as clinical condition library, medical conditions library, or simply as library. This library may be a part of a non-transient computer-readable medium, which may also contain a set of instructions that cause a computer to carry out all the steps of the present invention.

In one embodiment of the present invention, the machine findings may further be linked to a set options that may be available to a user through a user terminal, such as a computer, a monitor, a display. In other words, it may be possible to provide different possibilities to a user, from which the user may choose to generate a final finding or human-based finding. However, in case that the user finds the machine finding inaccurate and/or incorrect, the user may also reject or overrule the machine findings by selecting from a list of options an overruling statement, e.g. by selecting a box with the option "No".

Further, the information obtained from processing the medical data may then be supplied to the algorithms, which may retrieve information useful for adjusting their thresholds. In simple words, the human-based finding may serve as input to train the algorithms. In one embodiments, the human-based finding may serve as input for the algorithms to make predictions based on the characteristics of the human-based data. Further, the algorithms may be able to retrieve information that also allows the adjustment of recognition parameters for future medical data. In other words, the algorithms may execute a machine learning process following static program instructions, which allow them to make decisions and/or predictions based on a pattern recognition of the input data. It will be understood that the algorithm (or plurality of algorithms) constitutes a computer program comprising instructions, which are executed by a computer and cause the computer to carry out any the above explained steps.

The present invention also relates to the numbered embodiments provided below.

Below, method embodiments will be discussed. These embodiments are abbreviated by the letter "M" followed by a number. Whenever reference is herein made to "method embodiments", these embodiments are meant.

M1. A method for generating a report (50) comprising
receiving a user input to thereby generate at least one final finding (24);
automatically generating the report (50) based on the at least one final finding (24); and
utilizing the at least one final finding (24) to train at least one algorithm (12), wherein the at least one algorithm (12) is configured to generate at least one machine finding (22).

M2. The method according to the preceding embodiment, wherein the method further comprises
outputting at least one output machine finding (22) to a user (100);
and further wherein the user input is related to the at least one output machine finding (22) output to the user (100).

M3. The method according to any of the preceding embodiments, wherein the method is carried out by a data processing system.

M4. The method according to any of the preceding embodiments, wherein the method further comprises
at least one algorithm (12) generating the at least one output machine finding (22).

M5. The method according to the preceding embodiment, wherein the at least one output machine finding (22) is generated based on input data (10).

M6. The method according to the preceding embodiment, wherein the input data (10) is medical data.

M7. The method according to the preceding embodiment, wherein the medical data comprises medical imaging data.

M8. The method according to the preceding embodiment, wherein the medical imaging data is data retrieved by at least one of X-ray, magnetic resonance imaging, ultrasound, endoscopy, elastography, tactile imaging, thermography, medical photography and nuclear medicine functional imaging techniques as positron emission tomography (PET) and Single-photon emission computed tomography (SPECT).

M9. The method according to any of the preceding embodiments with the features of embodiment M6, wherein the medical data comprises data based on electroencephalography (EEG), magnetoencephalography (MEG), and/or electrocardiography (ECG).

M10. The method according to any of the preceding embodiments, wherein the report (50) is a medical report.

M11. The method according to any of the preceding embodiments with the features of embodiment M2, wherein the at least one output machine finding (22) is output to the user (100) before receiving the user input.

M12. The method according to any of the preceding embodiments with the features of embodiment M2, wherein the at least one output machine finding (22) is a plurality of output machine findings (22).

M13. The method according to the preceding embodiment, wherein the method further comprises storing the output machine findings (22) in a tree structure.

M14. The method according to any of the preceding embodiments, wherein the at least one final finding (24) is a plurality of final findings (24).

M15. The method according to the preceding embodiment, wherein the method further comprises storing the final findings (24) in a tree structure.

M16. The method according to any of the preceding embodiments, wherein the user input comprises a plurality of input data points.

M17. The method according to the preceding embodiment, wherein the input data points are computer-readable input data points.

M18. The method according to any of the 2 preceding embodiments, wherein the input data points comprise at least one select data point with one or more predetermined select options, wherein in the step of receiving a user input, the user selects one or more of the select options.

M19. The method according to any of the 3 preceding embodiments, wherein the input data points comprise at least one free text data point, wherein in the step of receiving a user input, the user provides a text.

M20. The method according to the preceding embodiment, wherein the user types the text.

M21. The method according to the preceding embodiment, wherein the user speaks the text into a microphone.

M22. The method according to any of the preceding embodiments with the features of embodiment M16, wherein the input data points comprises at least one probability input data point, and wherein at least one final finding is a probability finding.

M23. The method according to any of the preceding embodiments with the features of embodiment M2, wherein at least one output machine finding (22) is a probability finding.

M24. The method according to any of the preceding embodiments and with the features of embodiment M4, wherein the at least one algorithm (12) comprises a pattern recognition algorithm.

M25. The method according to any of the preceding embodiments and with the features of embodiment M3, wherein the data processing system comprises a user terminal (14) and a server.

M26. The method according to the preceding embodiment, wherein the user input is received by the user terminal (14).

M27. The method according to any of the preceding embodiments with the features of embodiment M25, wherein the report (50) is generated by the user terminal (14)

M28. The method according to any of the preceding embodiments with the features of embodiment M25, wherein the step of utilizing the at least one final finding (24) to train at least one algorithm (12) is performed by the server.

M30. The method according to any of the preceding embodiments with the features of embodiment M2, wherein the method further comprises generating the at least one output machine finding (22).

M31. The method according to the preceding embodiment and with the features of embodiment M25, wherein the step of generating the at least one output machine finding (22) is performed by the server.

M32. The method according to any of the preceding embodiments with the features of embodiment M25 and M2, wherein the user terminal (14) outputs the at least one output machine finding (22) to the user (100).

M33. The method according to any of the preceding embodiment and with the features of embodiment M25, wherein the data processing system further comprises a data input terminal.

M34. The method according to the preceding embodiment and with the features of embodiment M5, wherein the method further comprises inputting the input data (10) by means of the data input terminal.

M35. The method according to the preceding embodiment, wherein the method further comprises sending the input data (10) from the data input terminal to the server.

M36. The method according to the preceding embodiment, wherein the input data (10) is sent encrypted from the data input terminal to the server.

M37. The method according to the preceding embodiment, wherein the input data (10) is sent end-to-end encrypted.

M38. The method according to any of the preceding embodiments with the features of embodiment M31, wherein the at least one output machine finding (22) is sent from the server to the user terminal (14).

M39. The method according to any of the preceding embodiments with the features of embodiment M28, wherein the at least one final finding (24) is sent from the user terminal (14) to the server.

M40. The method according to any of the preceding embodiments with the features of embodiment M26, wherein at least a part of the communication between the server and the user terminal is encrypted.

M41. The method according to the preceding embodiment, wherein at least a part of the communication between the server and the user terminal is end-to-end encrypted.

Below is a list of system embodiments. Those will be indicated with a letter "S". Whenever such embodiments are referred to, this will be done by referring to "S" embodiments.

S1. A data processing system for generating a report (50) comprising:
- a receiving component for receiving a user input to thereby generate at least one final finding (24);
- a generating component for automatically generating the report (50) based on the at least one final finding (24); and
- a utilizing component for utilizing the at least one final finding (24) to train at least one algorithm (12), wherein the at least one algorithm (12) is configured to generate at least one machine finding (22).

S2. The system according to the preceding embodiment, wherein the system further comprises
- an outputting component configured to output at least one output machine finding (22) to a user (100).

S3. The system according to any of the preceding system embodiments, wherein the system further comprises
- at least one algorithm (12) configured to generate the at least one output machine finding (22).

S4. The system according to the preceding embodiment, wherein the at least one output machine finding (22) is based on input data (10) that is preferably fed into the algorithm (12).

S5. The system according to the preceding embodiment, wherein the input data (10) is medical data.

S6. The system according to the preceding embodiment, wherein the medical data comprises medical imaging data.

S7. The system according to the preceding embodiment, wherein the medical imaging data is data retrieved by at least one of X-ray, magnetic resonance imaging, ultrasound, endoscopy, elastography, tactile imaging, thermography, medical photography and nuclear medicine functional imaging techniques as positron emission tomography (PET) and Single-photon emission computed tomography (SPECT).

S8. The system according to any of the preceding system embodiments with the features of embodiment S5, wherein the medical data comprises data based on electroencephalography (EEG), magnetoencephalography (MEG), and/or electrocardiography (ECG).

S9. The system according to any of the preceding system embodiments, wherein the report (50) is a medical report.

S10. The system according to any of the preceding system embodiments, wherein the report (50) is in computer readable form.

S11. The system according to any of the preceding system embodiments, wherein the system comprises a user terminal (14).

S12. The system according to the preceding embodiment, wherein the user terminal (14) comprises the receiving component.

S13. The system according to any of the 2 preceding embodiments and with the features of embodiment S2, wherein the user terminal (14) comprises the outputting component.

S14. The system according to any of the 3 preceding embodiments, wherein the user terminal (14) comprises the generating component.

S15. The system according to any of the preceding system embodiments, wherein the system comprises a server.

S16. The system according to the preceding embodiment, wherein the server comprises the utilizing component.

S17. The system according to any of the preceding system embodiments, wherein the system further comprises a data input terminal.

S18. The system according to the preceding embodiment and with the features of embodiment S4, wherein the data input terminal is configured to receive the input data.

S19. The system according to any of the preceding system embodiments, wherein the system is configured to carry out the method according to any of the preceding method embodiments.

Below is a list of computer program embodiments. Those will be indicated with a letter "C". Whenever such embodiments are referred to, this will be done by referring to "C" embodiments.

C1. A computer program comprising instructions which, when the program is executed by a computer, cause the computer to carry out the method according to any of the preceding method embodiments.

Below is a list of computer storage embodiments. Those will be indicated with a letter "T". Whenever such embodiments are referred to, this will be done by referring to "T" embodiments.

T1. A non-transient computer-readable medium comprising instructions which, when executed by a computer, cause the computer to carry out the method according to any of the preceding method embodiments.

Below is a list of use embodiments. Those will be indicated with a letter "U". Whenever such embodiments are referred to, this will be done by referring to "U" embodiments.

U1. Use of the system according to any of the preceding system embodiments.

U2. Use according to the preceding embodiment for carrying out the method according to any of the preceding method embodiments.

BRIEF DESCRIPTION OF THE DRAWINGS

Embodiments of the present invention will now be described with reference to the Figures. These embodiments are intended to exemplify, and not to limit, the scope of the present invention.

FIG. 2 (a) to (c) depict exemplary outputs of a user terminal according to an embodiment of the present technology.

FIG. 3 (a) to (b) depict exemplary outputs of a user terminal according to an embodiment of the present technology.

FIG. 5 depicts an exemplary output window according to embodiments of the present technology.

DESCRIPTION OF EMBODIMENTS

Figure 1:
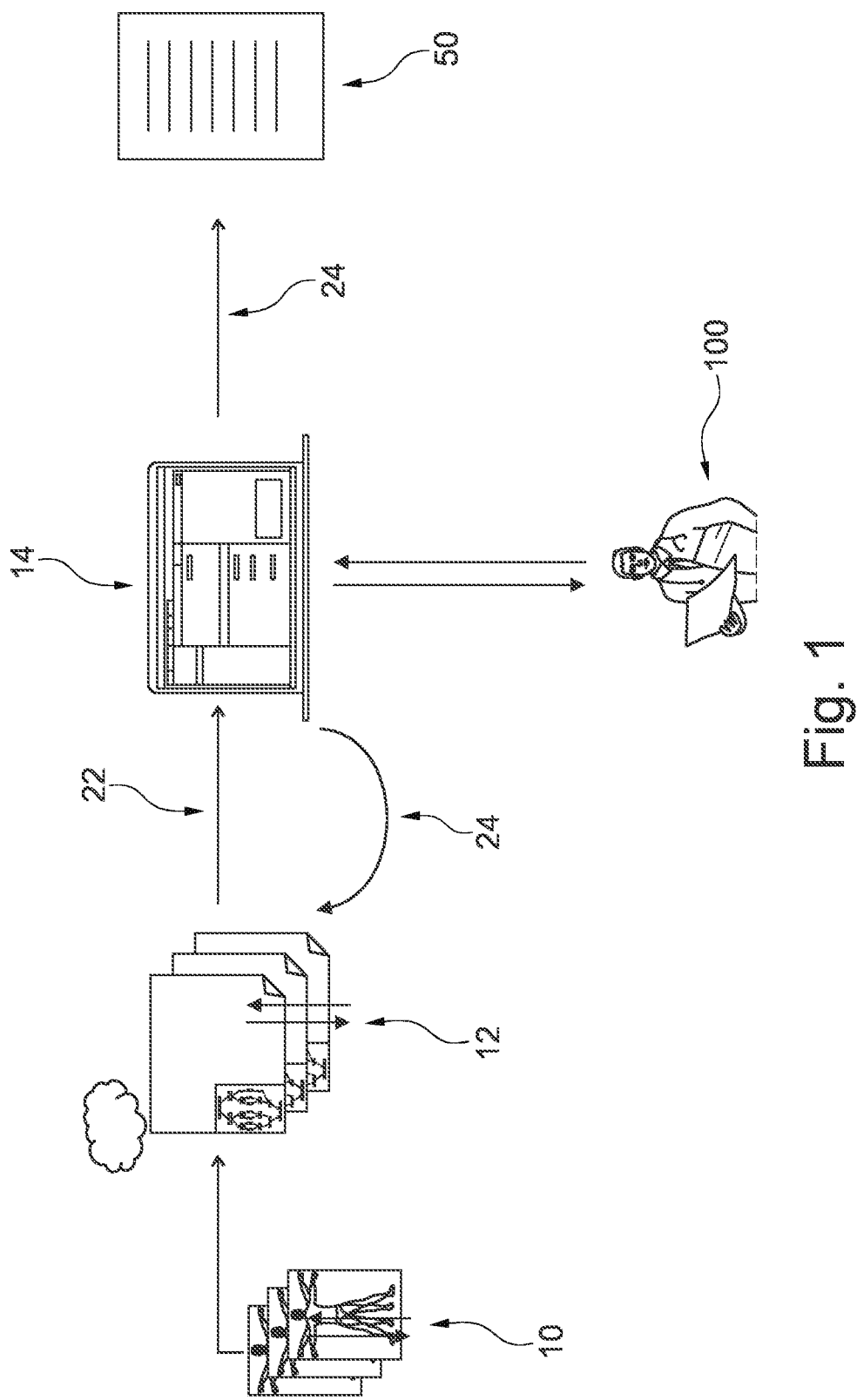
FIG. 1 illustrates a method and system according to an embodiment of the present technology.

In embodiments of the present technology, input data 10 is utilized. Input data 10 may be medical input data 10. In the embodiment depicted in FIG. 1, the input data 10 is image data 10, e.g., obtained by a medical imaging technique, such as X-ray, magnetic resonance imaging, ultrasound, endoscopy, elastography, tactile imaging, thermography, medical photography and nuclear medicine functional imaging techniques as positron emission tomography (PET) and Single-photon emission computed tomography (SPECT). While the present invention will be described with primary reference to medical imaging data as input data 10, it will be understood that also other data may be used as input data 10. For example, data based on electroencephalography (EEG), magnetoencephalography (MEG), and/or electrocardiography (ECG), may also be used as input data 10. Generally, any data that can be used to arrive at a (medical) finding may be used as input data 10.

The input data 10 is subjected to algorithms 12. That is, one or more algorithms 12 may be run with the input data 10. The aim of the algorithms 12 is to generate, based on the input data 10, findings 22, which will also be referred to as preliminary findings 22 or machine findings 22, as they have been automatically generated by an algorithm and not yet been checked by a medical professional 100. A medical professional 100 may also be referred to as medical personnel 100, medical practitioner 100, or simply as a user 100.

In other words, the algorithms 12 can scan the input data 10 in order to locate and identify the occurrence of distinctive and regularly repeated arrangements, and further transfer these arrangements into a set of findings 22. In more simple words, the algorithms 12 are in charge of searching and recognizing patterns and regularities in the input data 10, and subsequently associate them with a potential medical condition. Once the patterns in the input data 10 are completely processed, the algorithms 12 make them available as machine findings 22 and ready to get checked by the user 100.

As a mere example, the input data 10 may be image data of a patient's lung. An algorithm 12 may be run on or over this image data 10 and may indicate that the lung is enlarged, which would be the machine finding 22 in this example. The machine finding 22 may be output to the user 100 by using a user terminal 14. The user terminal 14 may be, e.g., a computer, a laptop, a smart phone, a tablet PC, and/or a smart speaker etc.

In other words, the input data 10, corresponding to image data of a patient's organ, is scanned and analyzed by algorithms 12, which may locate and recognize patterns within the input data 10. These patterns may be associated with potential medical conditions, for example, an enlarged lung. Then, the algorithm 12 makes the matched patterns accessible to a user 100 through a terminal 14.

For example, the machine finding 22 may be output to the user 100 by using a display. An exemplary output of such a machine finding 22 is depicted in FIG. 2 (a). Again, in the example, the machine finding 22 is that the lung is enlarged and this may be output to the user by ticking a respective box indicating the machine finding to the user 100. As the user 100 has not yet checked this finding, it may also be referred to as a preliminary finding. It may also be understood as a pre-selection done for the user 100. In the exemplary output depicted in FIG. 2 (a), the output may comprise a finding section 202 outputting the finding to the user and a checking section 204 outputting whether a finding has already been checked by the user 100, e.g., by a radiologist.

Before the user 100 has checked a machine finding, only the machine finding (also referred to as preliminary finding) may be output in finding section 202. In the discussed example, the user terminal 14 may output to the user that the Lung is enlarged (e.g., by checking a box "Yes" in finding section 202 to the question "Lung enlarged?"). The user terminal 14 may also output in section 204 that this finding has not yet been checked by the user (e.g., by checking a respective box "Not checked").

The user 100 may then check the respective machine finding 22. If agreeing to the machine finding, the user may simple leave the finding section 202 unaltered and click on a box labelled "Checked" in the checking section 204—an exemplary result of this is depicted in FIG. 2 (b). Thus, the user 100 may input that they agree with the machine finding 22.

If the user 100 does, however, not agree with the machine finding 22, she or he may "overrule" it. Referring again to the example of determining whether a lung is enlarged, the machine finding 22 may be that the lung is enlarged (see FIG. 2 (a)). If the user does not agree with this finding, they may click on the button "No" in the finding section 202. And the resulting output may be as depicted in FIG. 2 (c) indicating that the lung is not enlarged in the finding section 202 and that this finding is a finding that has already been checked by the user 100 in the checking section 204.

In one embodiment of the present invention, the algorithms 12 may also execute a subsequent in-depth further analysis of the identified patterns. In simple terms, a series of algorithms 12 may be triggered to identify sub patterns within an initial arrangement. That is, the algorithms 12 may further generate other machine findings providing finer screening of the input data 10. In other words, the algorithms 12 may execute a series of processes to extract and organize other characteristics of the patterns in the input data 10. Further, the algorithms 12 may be able to assign a specific medical condition, and the user 100 may later verify the veracity of this assignment.

The image data 10 apparently associated with a patient's lung medical condition is a case in point. The algorithms 12 may further identify other signs in the input data 10, which may give deeper insight regarding the potential medical condition of the patient's lung.

For instance, the input data 10 may indeed show an enlarged lung, which may have correctly been spotted by the algorithm 12. Moreover, the input data 10 may also display an additionally distinctive pattern within the enlarged section of the lung. To give an example, the enlarged portion of the lung may show characteristics associated to that of an altered tissue. Subsequently, the algorithm 12 may match other observed patterns to a specific type of lung enlargement (e.g. tumor), and may provide this information to the user 100. In other words, the algorithm 12 may output to the user 100, by means of the user terminal 14, findings 22 that indicate that the input data 10 contain characteristics that may suggest an enlarged lung. Once the user 100 corroborates the veracity of this information, e.g. by selection of a box "Yes" as depicted in FIG. 2 (a) in the finding section 202 to the question "Lung enlarged?", this selection automatically may trigger further options, as depicted in FIG. 3 (a). Such options may be a set of findings 22 that the algorithms 12 may display only in case that the first finding 22 is confirmed by the user 100 as correct. Now, the user 100 may access to a list of possible type of enlarged lungs, which the user 100 may choose from, e.g. the user 100 may, as depicted in FIG. 3 (a), select either "Tumor", "Hyperinflated" or simple leave the option open for a further user 100 by selecting an alternative box, that may, for example, be "Not specified". It will be understood that the further characteristics may also trigger other options such as dimensions (e.g. length, width), forms (oval, amorphous, irregular) or even further types of an already selected options. E.g. if the user 100 selects the option "Yes" for the question "Lung enlarged", and next selects the option "Tumor", then the user 100 may access to further given signs, as depicted in FIG. 3 (b), e.g. "Carcinoma" or "Sarcoma".

After the user 100 has checked the findings, they may be referred to as human-checked findings, human-based findings, final findings, or annotated findings (these terms can be used interchangeably). The human-based findings may be used twofold. First, they may be used as a feedback 24 to the algorithm 12. That is, the human-based findings 24 may be used to train the algorithm 12. Second, the human-based findings 24 may also form the basis for a report 50 that is automatically generated based on these human-based findings 24.

In other words, the human-based findings 24 may serve as foundations for a report 50. At the same time, the algorithms 12 may retrieve information from the human-based findings 24, which may be used to improve the machine finding by adjusting, correcting and/or expanding the pattern recognition process and the criteria for the association of a machine finding 22 to a specific medical condition. In one embodiment, the information retrieved from the human-based findings 24 may also be used to generate and/or provide further instructions and/or thresholds etc. for a given algorithm 12. Therefore, it will be understood that the information extracted from the human-based findings 24 may contribute to increase and improve future machine findings 22 that may be made available to the user 100.

In simple words, based on input data 10, the user 100 is provided with machine findings 22 generated by one or more algorithms 12 on a user terminal 14. The user 100 then checks these machine findings 22. Based on the machine findings 22 and by using the user's input, human-based findings 24 are generated. These human-based findings 24 are used to generate a medical report 50 and fed back to the algorithms 12 to train them.

It will be understood that the selection of options may be stopped at any of the steps and that a report 50 be immediately generated. Moreover, it will be understood that further users 100 (e.g. a further referring medical practitioner ad/or specialist), may retake the reporting of the machine findings 22. In other words, for instance, a first user 100 (e.g. a radiologist) may provide the input data 10 to the algorithms 12. Subsequently, the algorithms 12 process the input data 10 and generate a set of findings 22 that are made available to the first user 100, who may immediately start to check the findings 22 to generate a set of human-based findings 24. However, if the first user only proceeds until a certain step (in other words, the first user 100 does not check the full list of machine 22, but only the ones concerning their expertise), a report 50 may be generated, which may, next to the remaining findings 22, be made available to a second user 100 (e.g. an oncologist). Hence, the second user 100 may proceed to check the remaining machine findings 22, and a final report 50 with the specialist input may be generated. In other words, the algorithm 12 may always generate a set of machine findings 22 and human-based findings 24, which may be part of an output, e.g. as a report 50, and/or remain as a set of machine findings 22 and human-based findings 24, which can continue further checking by a next user 100 (e.g. a specialist on the field of the medical condition assigned to the findings 22 and 24, such as an oncologist).

It will be understood that the exact realization of providing the machine finding 22 to the user 100 and the user 100 checking the machine finding 22 and agreeing with it or overruling it is merely exemplary and that there are other embodiments realizing this in a different manner.

In one embodiment the machine finding 22 previously generated by algorithms may be complemented with further input provided by a user 100. The information supplied by a user 100 may be, inter alia, verification of machine finding 22, e.g. acceptation of the machine finding by selection a box "Yes" or rejection of the finding 22 by selecting a box "No". Moreover, the user 100 may also provide comments to unclear findings 22, and/or corrections to partially incomplete or incorrect machine finding 22.

That is, in embodiments of the present invention, one or more machine findings 22 are generated by one or more algorithms 12. The machine findings 22 are typically based on input data 10, such as medical image input data.

After their generation, the machine findings 22 are presented to a user 100 (and may therefore also be referred to as output machine findings 22). The user 100 provides additional input as regards the machine findings 22. In particular, the user 100 may confirm the machine findings 22 or may overrule the machine findings 22. Thus, user-based or final findings 24 are generated. The final findings (e.g., "The lung is enlarged.") may then be used to automatically generate a report 50, e.g., a medical report 50. Further, the final findings 24 may also be used to further train the algorithms 12. That is, the final findings 24 may be fed back to the algorithms 12 to improve them.

It will further be understood that this leads to the machine findings 12 and the input data 10 being annotated by the user 100. That is, after the user 100 has given their input resulting in the final finding 24, the input data 10 is annotated. E.g., if the input data 10 is medical imaging data 10, and the user 100 generate the final finding "The lung is enlarged", the medical imaging data 10 may be annotated with this finding.

Thus, a large amount of annotated data may be generated, improving the algorithms 12. For example, the algorithms 12 may be pattern recognition algorithms 12. It will be understood that such pattern recognition algorithms 12 typically rely on (a large amount of) annotated data. While it may be relatively simple to generate large amounts of annotated data for simple questions (e.g., "Is there a cat on a picture?"), this may be difficult for data requiring annotation by experts, such as medical doctors.

In the present technology, the user 100 is not specifically required to annotate data. To the contrary, the user is presented with a machine finding 22 intended to assist them in generating a report 50. As the user 100 intends to generate the report 50, they have an intrinsic motivation to check the machine finding 22 to thus generate a correct and full report 50.

However, at the same time, the user 100 thus annotates the data. In other words, the annotation can be seen as a by-product of the report generation.

That is, the present technology may allow to generate a large amount of annotated data used to further improve the algorithms 12.

It will be understood that the thus generated final findings 24 typically have a well defined and machine readable format. In the discussed example, one final finding 24 would represent the information that image data 10 depicts an enlarged lung. This would be input into the system as described with reference to FIG. 2. It will be understood that this results in a format of data that can readily be recognized by nearly any computer implemented system. Thus, the presently described technology results in relatively clean and well defined computer readable final findings 24, which can be readily used to further train and improve the algorithms 12. In other words, the final findings 24 used to generate the report 50 and to train the algorithms 24 may be discrete and defined data points (such as: "Lung enlarged?", "Tumor present?").

In one embodiment, these data points can be arranged in a tree structure. One optional configuration of this is also disclosed in WO 2016/135100 A1, which is incorporated by reference herein in its entirety.

Figure 4:
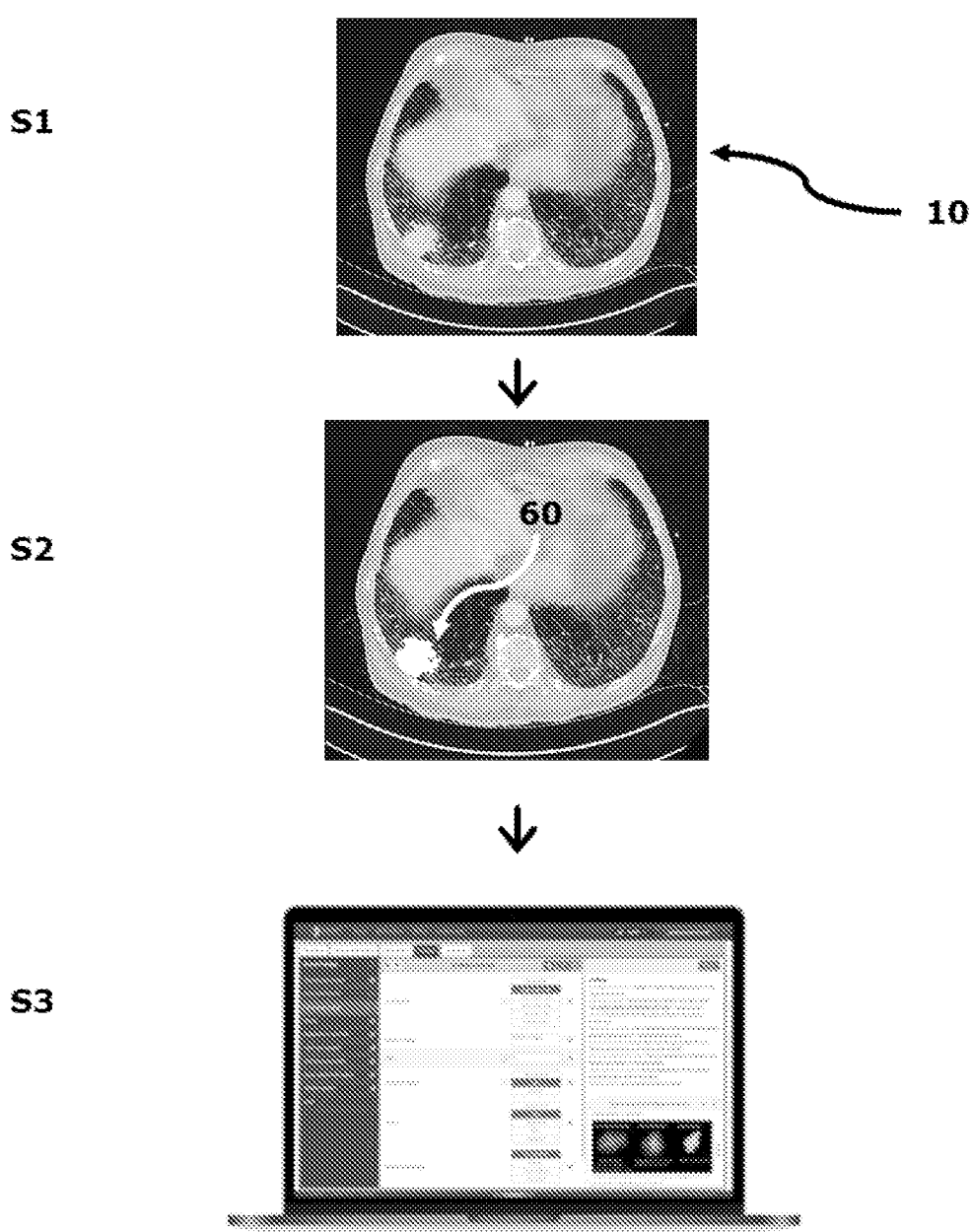
FIG. 4 depicts a use example of the present technology.

A further example of the present technology will now be discussed with reference to FIG. 4. FIG. 4 depicts different steps S1 to S3 according to embodiments of the present technology. In a first step S1, input data 10, e.g., CT image data 10, may be provided. Subsequently, in a step S2, the input data 10 may be subjected to algorithms to generate machine findings. In the embodiment depicted in FIG. 4, an algorithm may arrive at the machine finding that the input data 10 is indicative of pneumonia, e.g., in light of structure 60.

In turn, in a step S3, this machine finding may be output to a user, e.g., by displaying the machine finding to the user. A potential output of such machine findings is very schematically depicted in FIG. 4 (at step S3).

Figure 5:
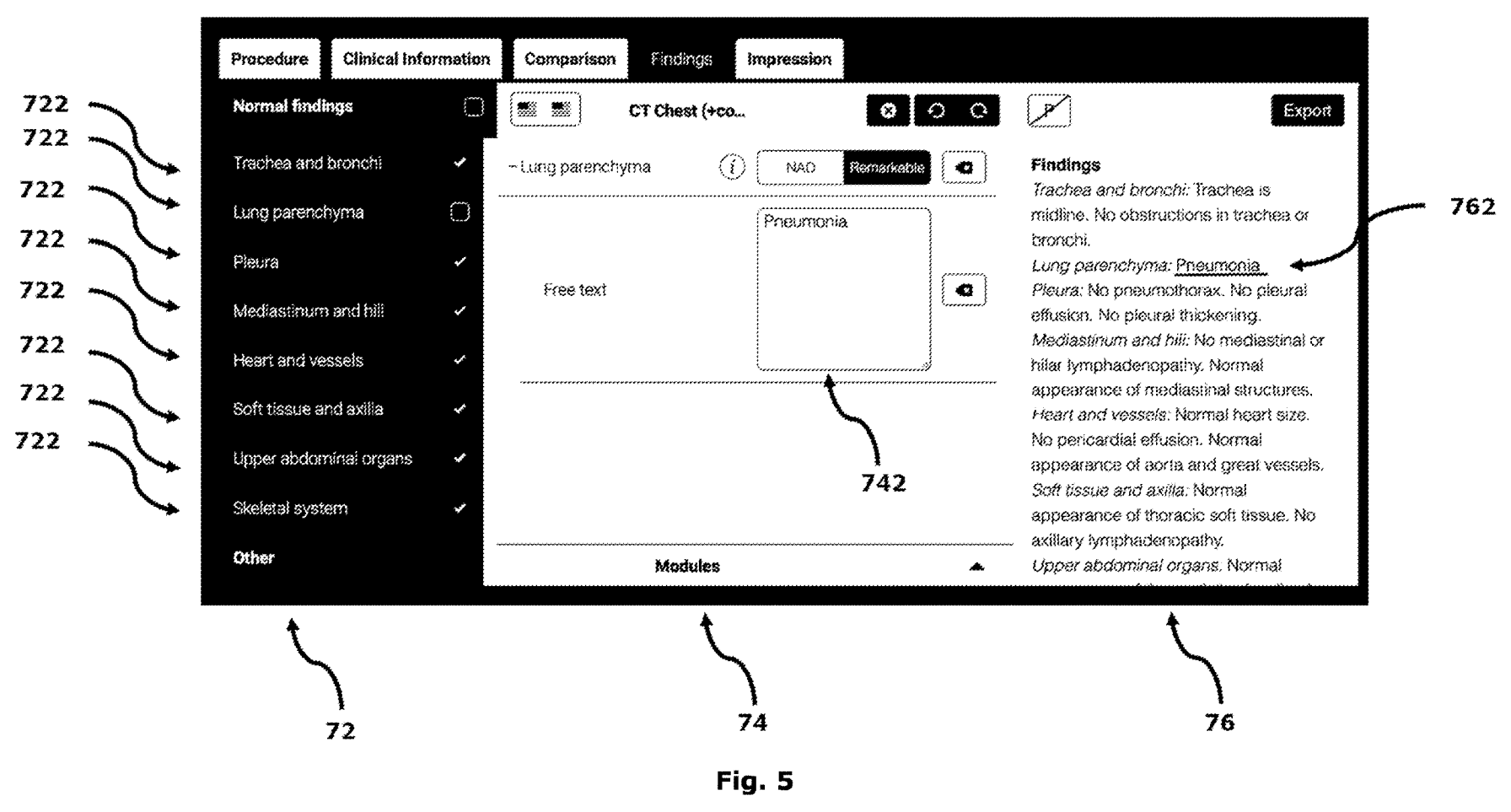

More details of such a potential output are also depicted in FIG. 5. More particularly, the data may be output in a data output element comprising different sections. In the depicted embodiment, the data output element comprises a module select section 72, a data correct section 74 and a report display section 76. In the module select section 72, the user may select different modules 722, which here relate to different tissues or tissue sections. In the presently depicted configuration, the "lung parenchyma" section is presently active and thus displayed in the data correct section 74.

As discussed in conjunction with FIG. 4, the algorithm may arrive at the machine finding that the input data is indicative of a pneumonia. This is displayed in the data correct section 74. More particularly, the data correct section may display the following machine findings to the user: Lung parenchyma: "Remarkable" (and not "NAD", denoting nothing abnormal detected) and "Pneumonia". Again, before the user has provided their feedback, such machine findings may also be considered to be preliminary only. The user may then consider these machine findings and approve or disapprove them. In the above, it has already been discussed how the approval or disapproval (which may also be referred to as a rejection or an overruling) may be effected.

However, as depicted in FIG. 5, the user input (leading to a final finding) may also be effected by using free text, i.e., by the user typing in the final finding in a respective box 742.

Further, FIG. 5 also depicts a report display section 76. The report display section 76 depicts a current status of a report that is generated based on the findings, which findings may be preliminary machine findings and/or final findings. In the depicted embodiment, a section affected by the current data correct section 74 is also highlighted, e.g., by underlining. Thus, when overruling a machine finding, the user is also provided with immediate feedback as regards how such an overruling or alteration of a preliminary finding will affect the final report.

For example, after being presented with the machine finding that there is a pneumonia present in the input data 10 (see FIG. 4), the user may overrule this finding. For example, the user may delete the term "Pneumonia" displayed in the box 742 of the data correct section 74 (see FIG. 5) and replace it with the term "Lung cancer". In turn, the respective report displayed in report display section 76 would also be altered, and the term "Pneumonia" would be replaced by the term "Lung cancer".

Further, this user based finding ("Lung cancer") may also be fed back to the algorithms, which may be artificial intelligence algorithms. As discussed, this may improve the accuracy of the algorithms.

In other words, embodiments of the present technology may provide a synoptic reporting system. In a reporting template, machine findings (of AI algorithms) are output and the user is requested to either approve or overrule the machine findings. Thus, machine readable report data is created, which may be fed back to the algorithms to further train and continuously improve them.

Generally, it should be understood that both the machine finding 22 and the final finding 24 do not necessarily have to be definite findings, i.e., in the form "Presence of pneumonia". Instead, one or both of the machine findings 22 and the final findings 24 can also be probability findings, i.e., non-definite findings, but findings that are expressed with a certain probability or likelihood.

E.g., in the above discussed example, the machine findings may be "Pneumonia: 80%", "Lung cancer: 20%". Further, the user may either approve these findings or overrule them. For example, the user findings may be "Pneumonia: 20%", "Lung cancer: 95%".

The report may either include these ratings as such. However, in alternative embodiments, the report may transform such ratings to respective wordings. For example, the above user or final findings may be transformed to a report stating "The findings are consistent with lung cancer. Pneumonia is less likely.". An exemplary mapping may be the following:

| Probability | Terminology |
|---|---|
| >90% | Consistent with |
| ~75% | Suspicious for/probable |
| ~50% | Possible |
| ~25% | Less likely |
| <10% | Unlikely |

Providing probability (also referred to as rated findings) may allow for more versatility and accuracy in the reports. Furthermore, it may remove interpretation problems that previously occurred when different users used terminology inconsistently.

Further, it may also improve training of the algorithms, as the user feedback may be more detailed.

Whenever a relative term, such as "about", "substantially" or "approximately" is used in this specification, such a term should also be construed to also include the exact term. That is, e.g., "substantially straight" should be construed to also include "(exactly) straight".

Whenever steps were recited in the above or also in the appended claims, it should be noted that the order in which the steps are recited in this text may be the preferred order, but it may not be mandatory to carry out the steps in the recited order. That is, unless otherwise specified or unless clear to the skilled person, the order in which steps are recited may not be mandatory. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

The invention claimed is:

1. A method for generating a report (50) carried out by a data processing system comprising a user terminal (14) and a server, wherein the method includes steps comprising:
   generating on the server using a first algorithm (12) based on input data (10) at least one first output machine finding (22);
   outputting the at least one first output machine finding (22) to a user (100);
   receiving a first user input in response to the at least one first output machine finding (22);
   based on the received user input and based on the input data (10) generating using the first algorithm (12) at least one second output machine finding providing further details on the first output machine finding (22);
   outputting the at least one second output machine finding to the user;
   receiving a second user input in response to the at least one second output machine finding;
   generating at least one final finding (24) based on the at least one first and the at least one second output machine finding and the first and second user input;
   automatically generating by the user terminal (14) the report (50) based on the at least one final finding (24); and utilizing the at least one final finding (24) to train the first algorithm (12), wherein the first algorithm (12) is configured to generate at least one further machine finding (22),
wherein the step of utilizing the at least one final finding (24) to train the first algorithm (12) is performed by the server.

2. The method according to claim 1, wherein the at least one final finding (24) is sent from the user terminal (14) to the server, wherein at least a part of the communication between the server and the user terminal is end-to-end encrypted.

3. The method according to claim 1, wherein the input data is medical imaging data.

4. The method according to claim 3, wherein the first algorithm (12) comprises a pattern recognition algorithm.

5. The method according to claim 1, wherein the at least one first and second output machine findings (22) are a plurality of output machine findings (22), wherein the method further comprises storing the plurality of output machine findings (22) in a tree structure, and further wherein the at least one final finding (24) is a plurality of final findings (24), wherein the method further comprises storing the plurality of final findings (24) in the tree structure.

6. The method according to claim 1, wherein the first and second user inputs comprise a plurality of input data points, wherein the plurality of input data points comprise at least one probability input data point, and wherein the at least one final finding is a probability finding.

7. The method according to claim 1, wherein the at least one first output machine finding (22) is a probability finding.

8. The method according to claim 1, wherein the first and second user inputs are received by the user terminal (14).

9. The method according to claim 8, wherein the method further comprises inputting the input data (10) by means of the user terminal.

10. The method according to claim 9, wherein the method further comprises sending the input data (10) from the user terminal to the server, wherein the input data (10) is sent end-to-end encrypted from the user terminal to the server.

11. The method according to claim 1, wherein the first and second user inputs are received by the user terminal (14), and wherein the user terminal (14) outputs the at least one first output machine finding (22) and the at least one second output machine finding (22) to the user (100).

12. A data processing system for generating a report (50) comprising:
a user terminal configured to perform:
an outputting component for outputting output machine findings to a user (100);
a receiving component for
receiving a first user input in response to at least one first output machine finding (22);
receiving a second user input in response to at least one second output machine finding; and
a first generating component for automatically generating the report (50) based on the at least one final finding (24); and
a server configured to perform
a second generating component for generating using a first algorithm (12) based on input data (10):
the at least one first output machine finding (22); and, based on the first user input, the at least one second output machine finding;
a third generating component for generating the at least one final finding (24) based on the received first and second user input; and
a utilizing component for utilizing the at least one final finding (24) to train the first algorithm (12), wherein the first algorithm (12) is configured to generate at least one further machine finding (22),
wherein the system is configured to carry out steps comprising:
generating on the server using the first algorithm (12) based on the input data (10) the at least one first output machine finding (22);
outputting by the user terminal the at least one first output machine finding (22) to the user (100);
receiving by the user terminal the first user input in response to the at least one first output machine finding (22);
based on the received first user input and based on the input data (10) generating on the server using the first algorithm (12) the at least one second output machine finding providing further details on the first output machine finding (22);
outputting by the user terminal the at least one second output machine finding to the user;
receiving by the user terminal the second user input in response to the at least one second output machine finding;
generating on the server the at least one final finding (24) based on the at least one first and the at least one second output machine finding and the first and second user input;
automatically generating by the user terminal (14) the report (50) based on the at least one final finding (24); and
utilizing the at least one final finding (24) to train the first algorithm (12), wherein the first algorithm (12) is configured to generate the at least one further machine finding (22), wherein the step of utilizing the at least one final finding (24) to train the first algorithm (12) is performed by the server.

* * * * *